US010959656B2

(12) United States Patent
Kanayama et al.

(10) Patent No.: US 10,959,656 B2
(45) Date of Patent: Mar. 30, 2021

(54) METHOD FOR SAMPLING CEREBRAL INSULAR CORTEX ACTIVITY

(71) Applicant: HIROSHIMA UNIVERSITY, Higashihiroshima (JP)

(72) Inventors: Noriaki Kanayama, Hiroshima (JP); Kai Makita, Hiroshima (JP); Takashi Sasaoka, Hiroshima (JP); Masahiro Machizawa, Hiroshima (JP); Tomoya Matsumoto, Hiroshima (JP); Shigeto Yamawaki, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 396 days.

(21) Appl. No.: 15/673,411

(22) Filed: Aug. 9, 2017

(65) Prior Publication Data

US 2018/0103887 A1   Apr. 19, 2018

(30) Foreign Application Priority Data

Aug. 10, 2016   (JP) .............................. JP2016-157238

(51) Int. Cl.
*A61B 5/16*   (2006.01)
*A61B 5/055*   (2006.01)
(Continued)

(52) U.S. Cl.
CPC .............. *A61B 5/165* (2013.01); *A61B 5/055* (2013.01); *A61B 5/316* (2021.01); *A61B 5/374* (2021.01);
(Continued)

(58) Field of Classification Search
CPC .......... A61B 2576/026; A61B 5/04004; A61B 5/055; A61B 5/7282
See application file for complete search history.

(56) References Cited

U.S. PATENT DOCUMENTS

| 5,503,149 A | * | 4/1996 | Beavin | ............... A61B 5/04021 600/411 |
| 5,724,987 A | * | 3/1998 | Gevins | .................... A61B 5/16 600/544 |

(Continued)

FOREIGN PATENT DOCUMENTS

| JP | 2005-058449 A | 3/2005 |
| JP | 2006-095266 A | 4/2006 |
| JP | 2011-120824 A | 6/2011 |

OTHER PUBLICATIONS

V. Litvak, J. Mattout, S. Kiebel, C. Phillips, R. Henson, J. Kilner, G. Barnes, R. Oostenveld, J. Daunizeau, "EEG and MEG Data Analysis in SPM8" 2010, pp. 1-25. (Year: 2010).*

(Continued)

*Primary Examiner* — Kibrom K Gebresilassie
(74) *Attorney, Agent, or Firm* — Maschoff Brennan

(57) ABSTRACT

Disclosed herein is a technique for observing the insular cortex activity by using electroencephalograms. A method for sampling cerebral insular cortex activity includes: recording electroencephalograms (EEGs) provided by a plurality of EEG electrodes; creating a three-dimensional model in the form of a mesh in which a subject's brain is decomposed into a plurality of sites according to the subject's brain structure and positioning the plurality of EEG electrodes by reference to an image representing the subject's brain and head structure; creating a forward model by modeling a correlation between the activities of the respective brain sites of the three-dimensional model and an electroencephalogram distribution of the positioned EEG electrodes; and associating, by reference to information about a region of interest measured by functional magnetic resonance imaging (fMRI) and the forward model, data about the electroencephalograms recorded with the cerebral activity of the region of interest.

7 Claims, 9 Drawing Sheets

CREATE ESTIMATED MODEL

(51) Int. Cl.
*A61B 5/00* (2006.01)
*A61B 5/316* (2021.01)
*A61B 5/374* (2021.01)
*A61B 5/378* (2021.01)
*G01R 33/48* (2006.01)
*A61B 5/291* (2021.01)
*A61B 34/10* (2016.01)

(52) U.S. Cl.
CPC .............. *A61B 5/378* (2021.01); *A61B 5/743* (2013.01); *A61B 5/7425* (2013.01); *G01R 33/4806* (2013.01); *G01R 33/4808* (2013.01); *A61B 5/291* (2021.01); *A61B 5/7246* (2013.01); *A61B 2034/105* (2016.02); *A61B 2576/026* (2013.01)

(56) References Cited

U.S. PATENT DOCUMENTS

| | | | | |
|---|---|---|---|---|
| 6,488,617 | B1* | 12/2002 | Katz | A61B 5/0482 600/26 |
| 2007/0202477 | A1* | 8/2007 | Nakagawa | A61B 5/14553 434/236 |
| 2008/0218472 | A1* | 9/2008 | Breen | G06F 3/015 345/156 |
| 2009/0312663 | A1* | 12/2009 | John | A61B 5/0476 600/544 |
| 2010/0049482 | A1* | 2/2010 | He | A61B 5/374 703/2 |
| 2013/0034277 | A1* | 2/2013 | Cecchi | G06F 19/321 382/128 |
| 2013/0109996 | A1* | 5/2013 | Turnbull | A61B 5/7264 600/544 |
| 2013/0281879 | A1* | 10/2013 | Raniere | A61B 5/167 600/558 |
| 2016/0113545 | A1* | 4/2016 | Kim | A61B 5/378 600/544 |
| 2018/0103887 | A1* | 4/2018 | Kanayama | A61B 5/7425 |
| 2018/0303370 | A1* | 10/2018 | Kanayama | A61B 5/055 |
| 2019/0357792 | A1* | 11/2019 | Machizawa | A61B 5/165 |
| 2020/0329322 | A1* | 10/2020 | Ramsay | H04R 29/00 |

OTHER PUBLICATIONS

D. Sabatinelli, P. J. Lang, A. Keil and M. M. Bradley, "Emotional Perception: Correlation of Functional MRI and Event-Related Potentials" 7 pgs. (Year: 2006).*

Delorme and Makeig, "EEGLAB: an open source toolbox for analysis of single-trial EEG dynamics including independent component analysis", Journal of Neuroscience Methods, vol. 134. Issue 1, Mar. 15, 2004, pp. 9-21.

Lange et. al., "International Affective Picture System," 2003.

Litvak et al., "EEG and MEG Data Analysis in SPM8", Computational Intelligence and Neuroscience, vol. 2011, Article ID 852961, doi:10.1155/2011/852961, 2011, pp. 1-32

* cited by examiner

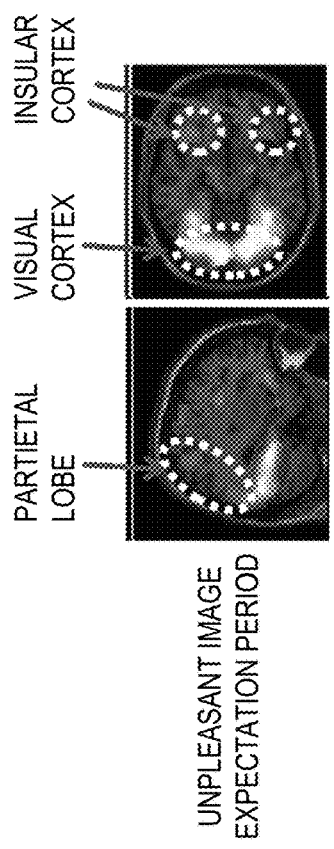
FIG. 2A
PLEASANT IMAGE EXPECTATION PERIOD
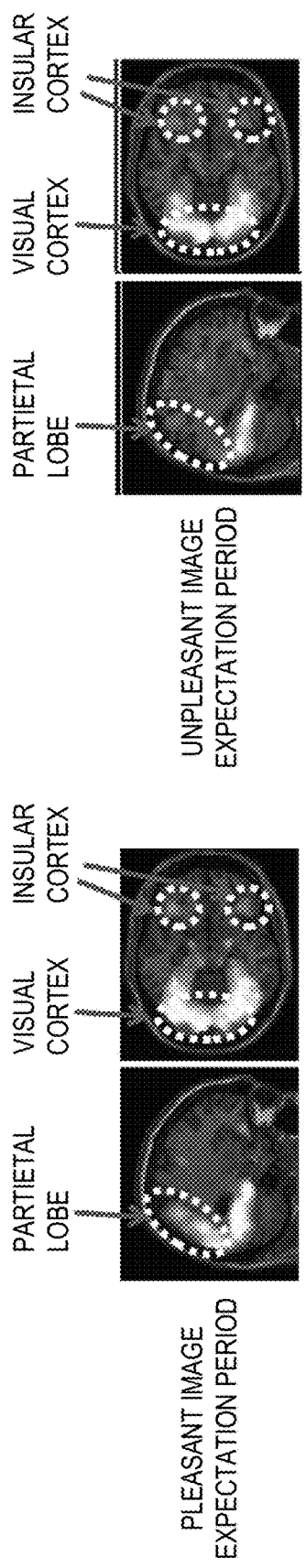
FIG. 2B
UNPLEASANT IMAGE EXPECTATION PERIOD
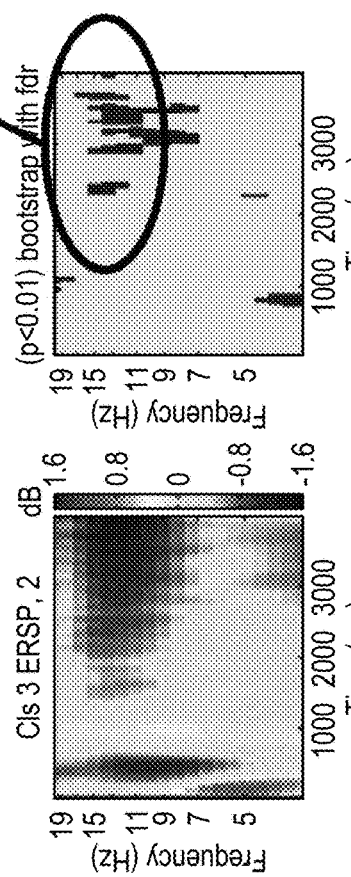
FIG. 3A
FIG. 3B
FIG. 3C
FIG. 3D

RECORD

DISTRIBUTION OF RAW WAVEFORMS

NOISE DETECTION BY INDEPENDENT COMPONENTS

DECOMPOSITION BY INDEPENDENT COMPONENT ANALYSIS

INDIVIDUAL MRI STRUCTURAL IMAGE

BACK-PROJECTION OF COMPONENTS

METHOD FOR SAMPLING CEREBRAL INSULAR CORTEX ACTIVITY

CROSS-REFERENCE TO RELATED APPLICATION

This application claims priority to Japanese Patent Application No. 2016-157238 filed on Aug. 10, 2016, the entire disclosure of which is hereby incorporated by reference.

BACKGROUND

The present disclosure relates to a method for measuring cerebral insular cortex activity.

A human being feels a sense of excitement, exhilaration, or suspense, or feels a flutter, on seeing or hearing something or on touching something or being touched by someone.

These senses are not mere emotions or feelings but brought about by complex, higher cerebral activities in which exteroception entering the brain through a somatic nervous system including motor nerves and sensory nerves, interoception based on an autonomic nervous system including sympathetic nerves and parasympathetic nerves, memories, experiences, and other factors are deeply intertwined with each other. The present inventors grasp these complex, higher cerebral functions such as the senses of exhilaration, suspense, and flutter, which are distinctly different from mere emotions or feeling, as "sensibilities" comprehensively. The present inventors also consider the sensibilities a higher cerebral function of synthesizing together the exteroceptive information (somatic nervous system) and the interoceptive information (autonomic nervous system) and looking down upon an emotional reaction produced by reference to past experiences and memories from an even higher level. In other words, the "sensibility (Kansei)" can be said to be a higher cerebral function allowing a person to intuitively sense the gap between his or her prediction (image) and the result (sense information) by comparing it to his or her past experiences and knowledge.

Viewing the sensibility (Kansei) that is such a higher cerebral function in perspective requires grasping the sensibility (Kansei) comprehensively from various points of view or aspects.

For example, the sensibility (Kansei) may be grasped from a "pleasant/unpleasant" point of view or aspect by determining whether the person is feeling fine, pleased, or comfortable, or otherwise, feeling sick, displeased, or uncomfortable.

Alternatively, the sensibility (Kansei) may also be grasped from an "active/inactive" point of view or aspect by determining whether the person is awaken, heated, or active, or otherwise, absent-minded, calm, or inactive.

Still alternatively, the sensibility (Kansei) may also be grasped from a "sense of expectation" point of view or aspect by determining whether the person is excited with the expectation or anticipation of something, or otherwise, bitterly disappointed and discouraged.

A Russell's circular ring model, plotting the "pleasant/unpleasant" and "active/inactive" parameters on dual axes, is known. The feelings can be represented by this circular ring model.

Meanwhile, there are a large number of prior documents mentioning the sensibility (Kansei), all of which consider sensibilities synonymous with feelings without sharply distinguishing the former from the latter. For example, Japanese Unexamined Patent Publication No. 2006-95266 regards sensibilities as including feelings and intensions and discloses a method for quantitatively measuring the sensibility (Kansei) state of a person who is happy, sad, angry, or glad, for example. However, Japanese Unexamined Patent Publication No. 2006-95266 does not distinguish sensibilities from feelings, and fails to teach evaluating the sensibility (Kansei) from the time-axis (sense of expectation) point of view.

Japanese Unexamined Patent Publication No. 2011-120824 (see, in particular, claim 5) discloses a method for quantitatively evaluating a plurality of sensibilities to be pleasure, displeasure, and so forth, by making a principle component analysis on biometric information about a subject given some stimulus corresponding to pleasure, displeasure, or any other sensibility (Kansei) for learning purposes.

Japanese Unexamined Patent Publication No. 2005-58449 discloses an apparatus for visualizing feeling data as feeling parameter values using a feeling model such as a dual-axis model or a triple-axis model. However, as is clear from its description stating that sensibility (Kansei) cannot be evaluated quantitatively, Japanese Unexamined Patent Publication No. 2005-58449 mixes up feelings and sensibilities, and neither teaches nor suggests the time axis (sense of expectation).

Japanese Unexamined Patent Publication No. 2005-58449 forms feeling models using a first axis indicating the degree of closeness of a person's feeling to either pleasure or displeasure, a second axis indicating the degree of closeness of his or her feeling to either an excited or tense state or a relaxed state, and a third axis indicating the degree of closeness of his or her feeling to either a tight-rope state or a slackened state, and discloses a method for expressing his or her feeling status using feeling parameters indicated as coordinate values in the three-axis space. However, these are nothing but models for expressing feelings and just a complicated version of the Russell's circular ring model.

As can be seen from the foregoing description, the techniques disclosed in these prior documents all stay within the limits of feeling analysis, and could not be used to evaluate the sensibilities properly.

The sensibility (Kansei) is a higher cerebral function of comparing the gap between the prediction (image) and the result (sense information) to experiences and knowledge, and therefore, cannot be sufficiently expressed by the traditional circular ring model comprised of the two axes indicating pleasure/displeasure and activity/inactivity. Thus, the present inventors advocate a multi-axis sensibility (Kansei) model in which the time axis (indicating a sense of expectation, for example) is added as a third axis to the Russell's circular ring model.

It is generally known that insular cortex is involved in forming the interoceptive information. Observing the cerebral activities about the interoception is one of important steps of the study in sensibility (Kansei). The sensibilities involve not only evaluation of information about the external environment but also individuality indicating how the person has grasped the information by him- or herself. Thus, the sensibilities are believed to be a decision made based on the perception of the interoception including the autonomic nervous system described above.

According to the results of the researches carried out so far by the present inventors, as for the third axis of the multi-axis sensibility (Kansei) model advocated by the present inventors, among other things, as for the pleasant image expectation and unpleasant image expectation that are specific indices to the sense of expectation, the insular cortex activities could be detected by functional magnetic resonance imaging (fMRI) but could not be observed in electroencephalograms (EEG).

The present disclosure provides a technique for observing the insular cortex activity by using electroencephalograms.

SUMMARY

A method for sampling cerebral insular cortex activity according to an aspect of the present disclosure includes: recording electroencephalograms (EEGs) provided by a plurality of EEG electrodes; creating a three-dimensional model in the form of a mesh in which a subject's brain is decomposed into a plurality of sites according to the subject's brain structure and positioning the plurality of EEG electrodes by reference to an image representing the subject's brain and head structure; creating a forward model by modeling a correlation between the activities of the respective brain sites of the three-dimensional model and an electroencephalogram distribution of the positioned EEG electrodes; and associating, by reference to information about a region of interest measured by functional magnetic resonance imaging (fMRI) and the forward model, data about the electroencephalograms recorded with the cerebral activity of the region of interest.

According to the present disclosure, using (i) a forward model, created by modeling a correlation between a three-dimensional model of a subject's brain modified according to his or her brain structure and an electroencephalogram distribution of EEG electrodes positioned by reference to an image representing the subject's brain and head structure, and (ii) information about a region of interest measured by fMRI allows recorded electroencephalogram data provided by the EEG electrodes to be associated with the cerebral activity of the region of interest, thus providing a technique for ultimately sampling cerebral insular cortex activity. This greatly contributes toward unraveling the sense of interoception, including the autonomic nervous system, by using the electroencephalograms.

BRIEF DESCRIPTION OF THE DRAWINGS

FIGS. 2A and 2B show fMRI images representing sagittal and horizontal sections of a subject's brain.

FIGS. 3A-3D show, using EEGs, how a cerebral activity is caused by the posterior cingulate gyms as a signal source.

DETAILED DESCRIPTION

Embodiments of the present disclosure will be described in detail with reference to the drawings as needed. Note that excessively detailed description will sometimes be omitted herein to avoid complexity. For example, detailed description of a matter already well known in the art and redundant description of substantially the same configuration will sometimes be omitted herein. This will be done to avoid redundancies in the following description and facilitate the understanding of those skilled in the art.

Note that the present inventors provide the following detailed description and the accompanying drawings only to help those skilled in the art fully appreciate the present disclosure and do not intend to limit the scope of the subject matter of the appended claims by that description or those drawings.

Measurement of Insular Cortex by fMRI

First of all, an experiment is carried out in which 27 participants are presented with stimulus images that will evoke their emotions to evaluate the feeling states of those participants who are viewing those images. As the stimulus images, 80 emotion-evoking color images, extracted from IAPS (International Affective Picture System, Lange et. al., 2003), are used. Those 80 images include pleasant and unpleasant images.

Figure 1:
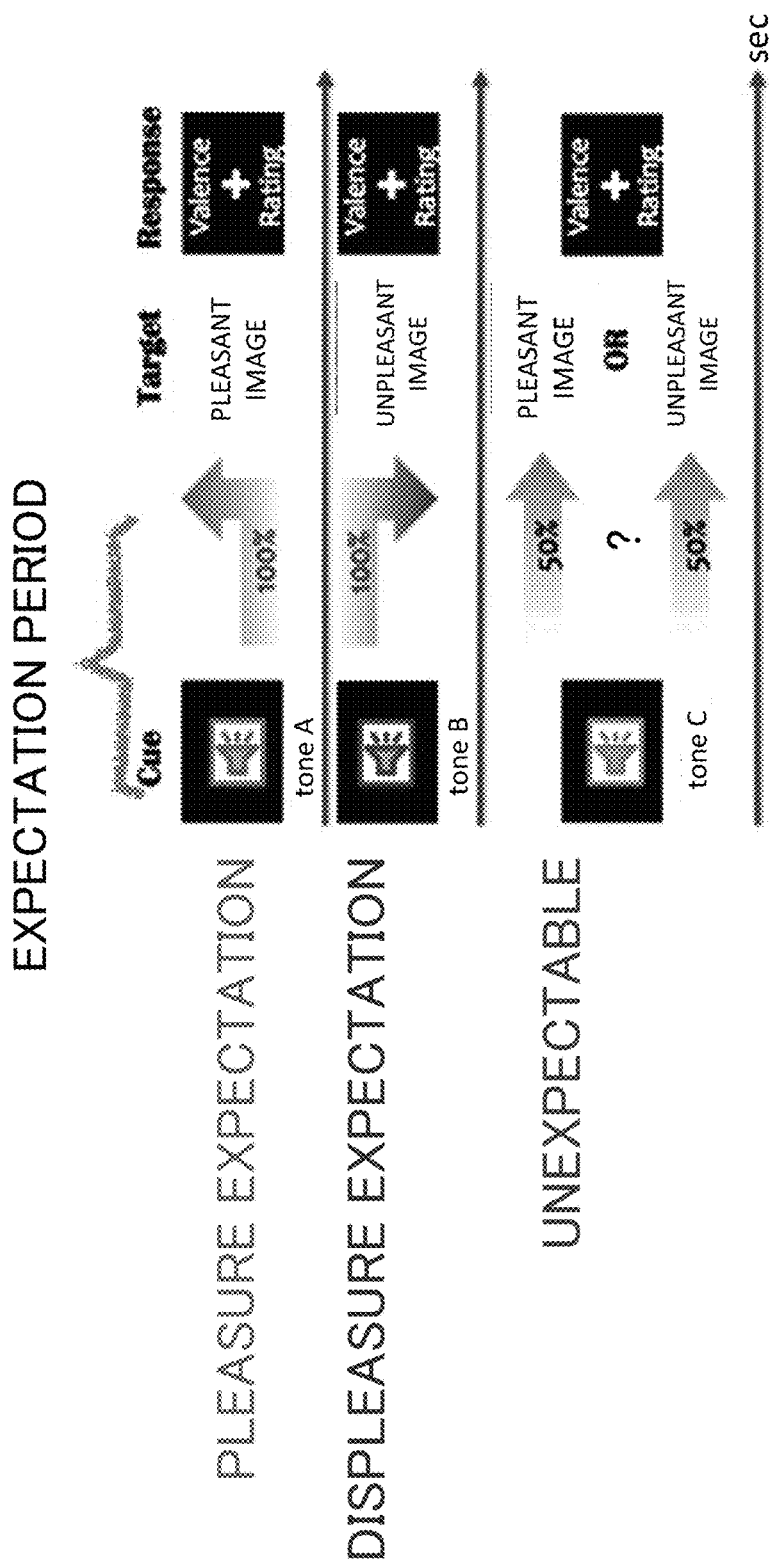
FIG. 1 illustrates generally how to carry out an experiment of presenting pleasant/unpleasant stimulus images.

FIG. 1 illustrates generally how to carry out the experiment of presenting the participants with those pleasant/unpleasant stimulus images. Each of those stimulus images will be presented on the computer screen. Then, the participants are each urged to answer pleasant or unpleasant. In this experiment, a pleasant image is presented to the participants every time tone A has been emitted; an unpleasant image is presented to the participants every time tone B has been emitted; and either a pleasant image or an unpleasant image is presented at a probability of 50% after tone C has been emitted. For example, each tone was specified by frequency.

In this experiment, that interval between a point in time when any of these three types of tones is emitted and a point in time when the image is presented is a period in which the participants expect what will happen next (i.e., presentation of either a pleasant image or an unpleasant image in this experiment). Their cerebral activities are observed during this expectation period. For example, when tone A is emitted, the participants are in the state of "pleasant image expectation" in which they are expecting to be presented with a pleasant image. On the other hand, when tone B is emitted, the participants are in the state of "unpleasant image expectation" in which they are expecting to be presented with an unpleasant image. Meanwhile, when tone C is emitted, the participants are in a "pleasant/unpleasant unexpectable state" in which they are not sure which of the two types of images will be presented, a pleasant image or an unpleasant image.

FIGS. 2A and 2B show fMRI images representing sagittal and horizontal sections of a subject's brain in the pleasant image expectation state (shown in FIG. 2A) and in the unpleasant image expectation state (shown in FIG. 2B). As indicated clearly by the dotted circles in FIGS. 2A and 2B, it can be seen that according to fMRI, brain regions including the parietal lobe, visual cortex, and insular cortex are involved in the pleasant image expectation and unpleasant image expectation, but that no difference is seen in the visual cortex and insular cortex between the pleasant image expectation and the unpleasant image expectation. This means that fMRI cannot distinguish the pleasant image expectation from the unpleasant image expectation.

Measurement of Insular Cortex with EEGs

FIGS. 3A-3D show, using EEGs, how a cerebral activity is caused by the posterior cingulate gyms as a signal source. FIG. 3A illustrates a sagittal cross section of the subject's brain and also shows the signal source distribution of respective independent components (as indicated by the dotted circle). FIG. 3B shows a result of a time-frequency analysis that was carried out on a signal of the EEG signal source during the pleasant image expectation period. FIG. 3C shows a result of a time-frequency analysis that was carried out on a signal of the EEG signal source during the unpleasant image expectation period. Furthermore, FIG. 3D shows a time-frequency region in which there was a difference when the pleasant image expectation and unpleasant image expectation were compared to each other. In FIG. 3D, the dark regions indicate the time-frequency regions with the difference. In FIG. 3D, a clear difference was observed in the encircled region. These EEG measurement results reveal that reactions in the α to β bands of the parietal lobe were involved in the pleasant image expectation.

Figure 4D:
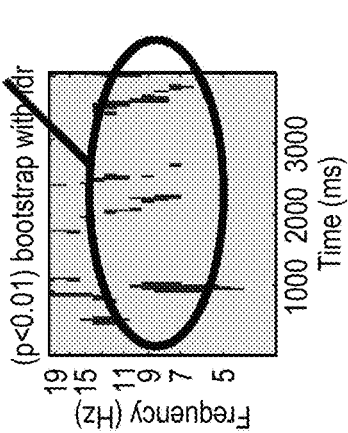
FIGS. 4A-4D show, using EEGs, how a cerebral activity is caused by signal sources distributed over brain sites ranging from the visual cortex through the cerebellar.
Figure 4C:
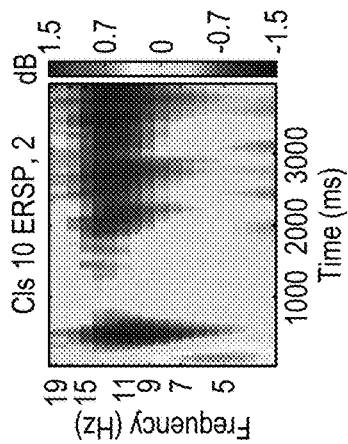
Figure 4B:
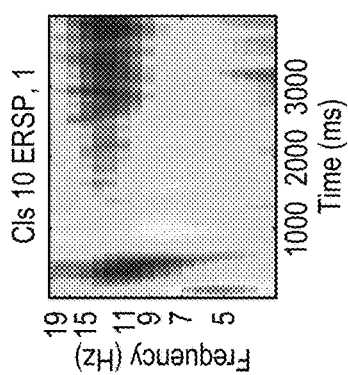
Figure 4A:
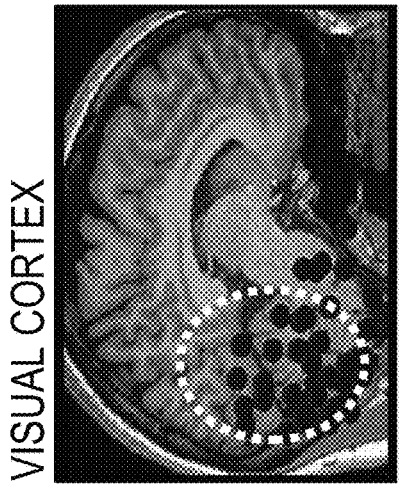

FIGS. 4A and 4D show, using EEGs, how a cerebral activity is caused by signal sources distributed over brain sites ranging from the visual cortex through the cerebellar. FIG. 4A illustrates a sagittal cross section of the subject's brain and also shows the signal source distribution of respective independent components (as indicated by the dotted circle). FIG. 4B shows a result of a time-frequency analysis that was carried out on a signal of the EEG signal source during the pleasant image expectation period. FIG. 4C shows a result of a time-frequency analysis that was carried out on a signal of the EEG signal source during the unpleasant image expectation period. Furthermore, FIG. 4D shows a time-frequency region in which there was a significant difference when the pleasant image expectation and unpleasant image expectation were compared to each other. In FIG. 4D, the encircled region indicates a region that seems to be characteristic. These EEG measurement results reveal that reactions in the α band, of which the signal sources were distributed over the brain sites ranging from the visual cortex to the cerebellar, were involved in the pleasant image expectation.

These are estimated EEG signal sources representing significant differences between the pleasant image expectation and the unpleasant image expectation, which did not cover the insular cortex.

Embodiment of the Present Disclosure

According to an embodiment of the present disclosure, an insular cortex activity by estimating the EEG signal sources can be sampled by performing the following steps:

[Step 1] Recording Electroencephalograms

Figure 5:
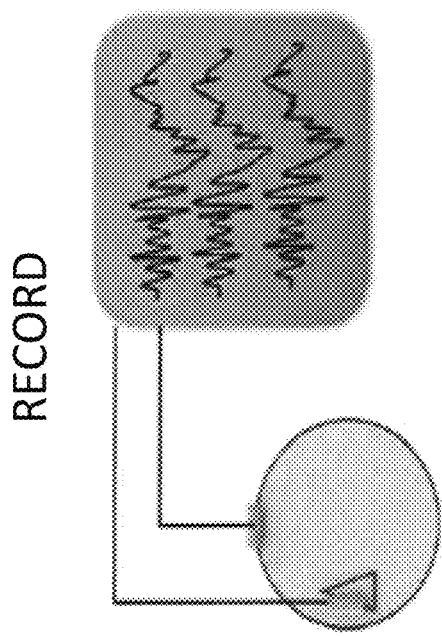
FIG. 5 illustrates how to record electroencephalograms provided by a plurality of EEG electrodes.
Figure 6:
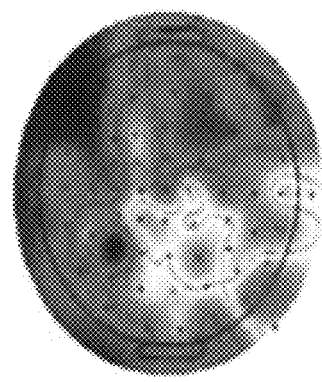
FIG. 6 illustrates the distribution of raw waveforms of electroencephalograms at a certain point in time.

First of all, electroencephalograms provided by a plurality of (e.g., 64) EEG electrodes are recorded as shown in FIG. 5. In the electroencephalograms, the abscissa indicates the time and the ordinate indicates the amplitude. On each of these electroencephalograms, various components that are unrelated to the cerebral activity, including blink and power supply noise, are superposed. FIG. 6 illustrates the distribution of raw waveforms of electroencephalograms at a certain point in time. In FIG. 6, the shades indicate the amplitude.

[Step 2] Decomposition by Independent Component Analysis

Figure 7:
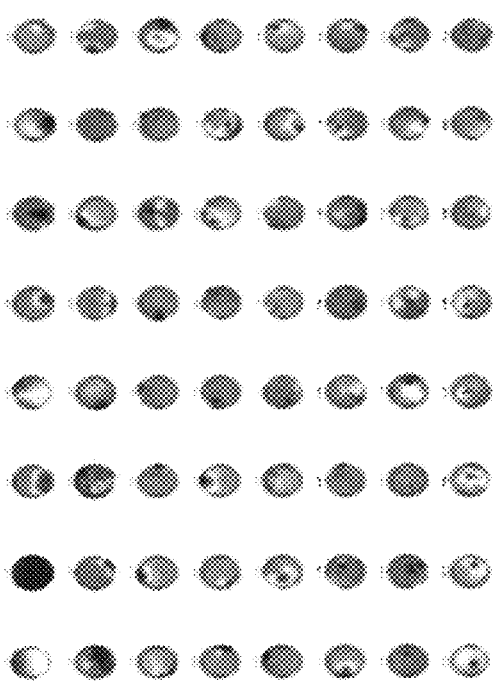
FIG. 7 shows a distribution of 64 independent components on the scalp.

The recorded electroencephalograms provided by the 64 EEG electrodes are decomposed into 64 independent components by independent component analysis (e.g., by the Logistic Informax method). Specifically, calculating a weight matrix for performing such a transform as to maximize the degree of independence in the signals measured by the respective EEG electrodes and then multiplying the signals of the respective EEG electrodes by the weight matrix allow the electroencephalograms to be transformed into independent component data. FIG. 7 shows a distribution of 64 independent components on the scalp. In FIG. 7, the shades indicate the amplitude. Step 2 may be performed on a toolbox for processing electrophysiological data (see, for example, A. Delorme and S. Makeig, "EEGLAB: an open source toolbox for analysis of single-trial EEG dynamics including independent component analysis," Journal of Neuroscience Methods, vol. 134, no. 1, pp. 9-21, 2004).

[Step 3] Noise Detection by Independent Components

Figure 8:
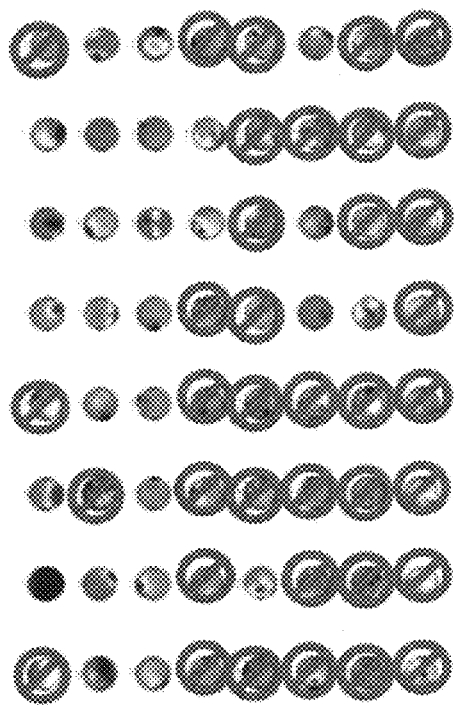
FIG. 8 illustrates how some independent components are detected as noise components.

A time-frequency power value is calculated on the basis of each independent component separated to detect independent components that are determined to be noise based on the bias of the distribution on the scalp, variance of the frequency power values, and other factors. FIG. 8 illustrates how some independent components have been detected as noise components. For example, (a) components with significant potential differences, (b) components involved with only a single EEG electrode, and other components are determined to be noise. Specifically, after the waveforms of respective independent components have been subjected to a frequency analysis and plotted as a spectrogram, the power of the spectrum could be significantly high in a frequency range to be affected by AC outlet noise or in a frequency range to be affected by myoelectric noise, or no peaks may be observed in a frequency range which is generally supposed to expand due to the electroencephalograms. When any of these situations arises, a determination is made, using, as indices, the kurtosis of the inverse matrix of the weighted matrix obtained by the independent component analysis, the distortion of an extreme distribution, and the residual variance during dipole estimation, whether or not it is a noise component.

[Step 4] Back-Projection of Components

Figure 9:
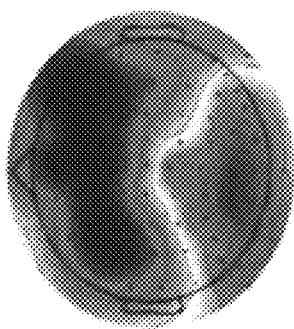
FIG. 9 shows a distribution of raw waveforms of electroencephalograms restored by the back-projection of components at a certain point in time.

Reducing the weight, added to the independent components determined to be noise components, to zero and back-projecting such zero-weight independent components onto electroencephalogram information on an electrode basis allow the data to be restored into waveform data, from which only noise components, having the same electrode and time information as the recorded electroencephalograms provided by the 64 EEG electrodes, have been removed. FIG. 9 shows a distribution of raw waveforms of electroencephalograms restored by the back-projection of components at a certain point in time. In FIG. 9, the shades indicate the amplitude. In this case, 38 components are determined to be noise components. Thus, the waveform distribution obtained in this step has been generated based on the other 26 components, and has had those noise components removed.

[Step 5] Capturing Individual MRI Structural Images

Figure 10:
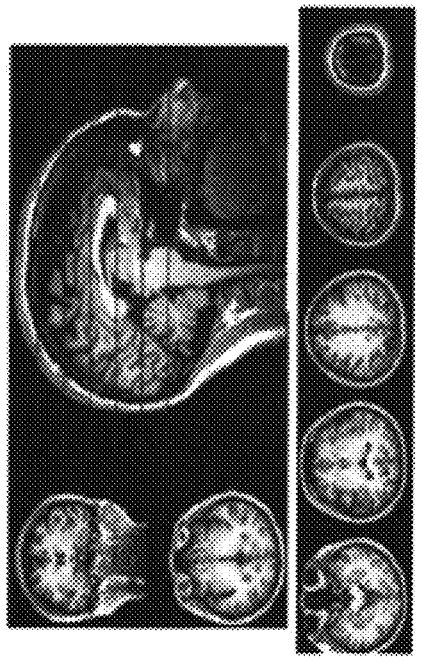
FIG. 10 shows Mill structural images of a subject's brain.

As shown in FIG. 10, MRI structural images of a subject's brain are captured. The brain size and the brain's organizational structure (such as the spinal fluid and the separation membrane of the brain) vary from one subject to another. In addition, the propagation rate of the brain wave also varies depending on the organizational difference. That is why measurements of individual brain shapes are used to establish a brain wave propagation model.

[Step 6] Creating Brain Mesh Patch

Figure 11:
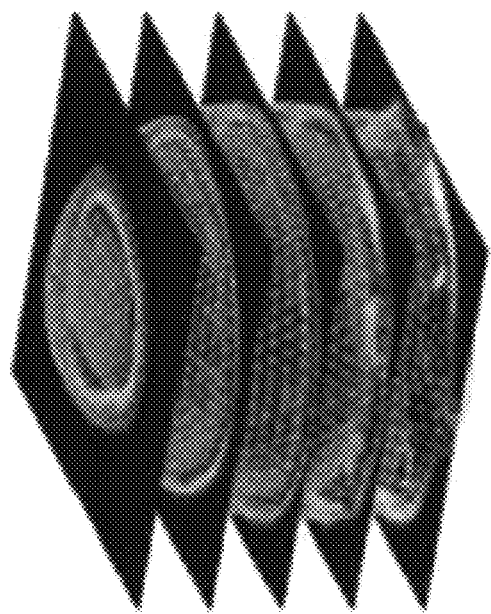
FIG. 11 illustrates a multilayer brain mesh patch.

As shown in FIG. 11, a brain structural model, i.e., a multilayer brain mesh patch, is created based on an MRI structural image representing each subject's brain. In FIG. 11, only five layers are shown for convenience sake. In this step, a meshed three-dimensional brain model is created based on the subject brain's MRI structural image obtained in Step 5. In this example, a mesh model, in which 8,196 current sources were set in the brain to be respective nodes and connected together at their edges, was used. FIG. 11 schematically illustrates this state.

[Step 7] Positioning Electrodes

Figure 12:
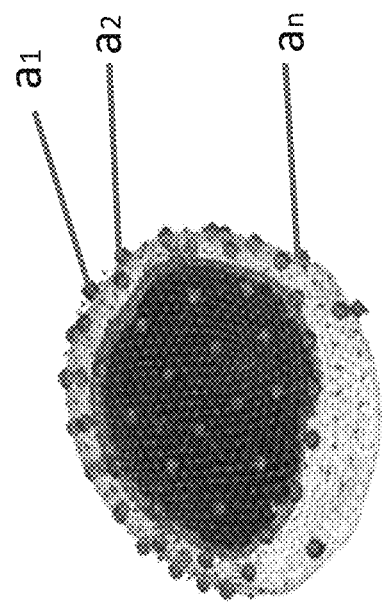
FIG. 12 illustrates how EEG electrodes have been positioned in accordance with the subject's brain structure.

With respect to the brain's structural model, the positions of the EEG electrodes actually set on the scalp are registered. This step is carried out to adjust the positions of the EEG electrodes according to the organizational structure and shape of the brain. FIG. 12 illustrates a state where EEG electrodes have been positioned. In FIG. 12, $a_1$, $a_2$, ... and $a_n$ denote respective EEG electrodes. FIG. 12 illustrates how the respective EEG electrodes have been positioned according to the brain's size and structure.

[Step 8] Creating Forward Model

Figure 13:
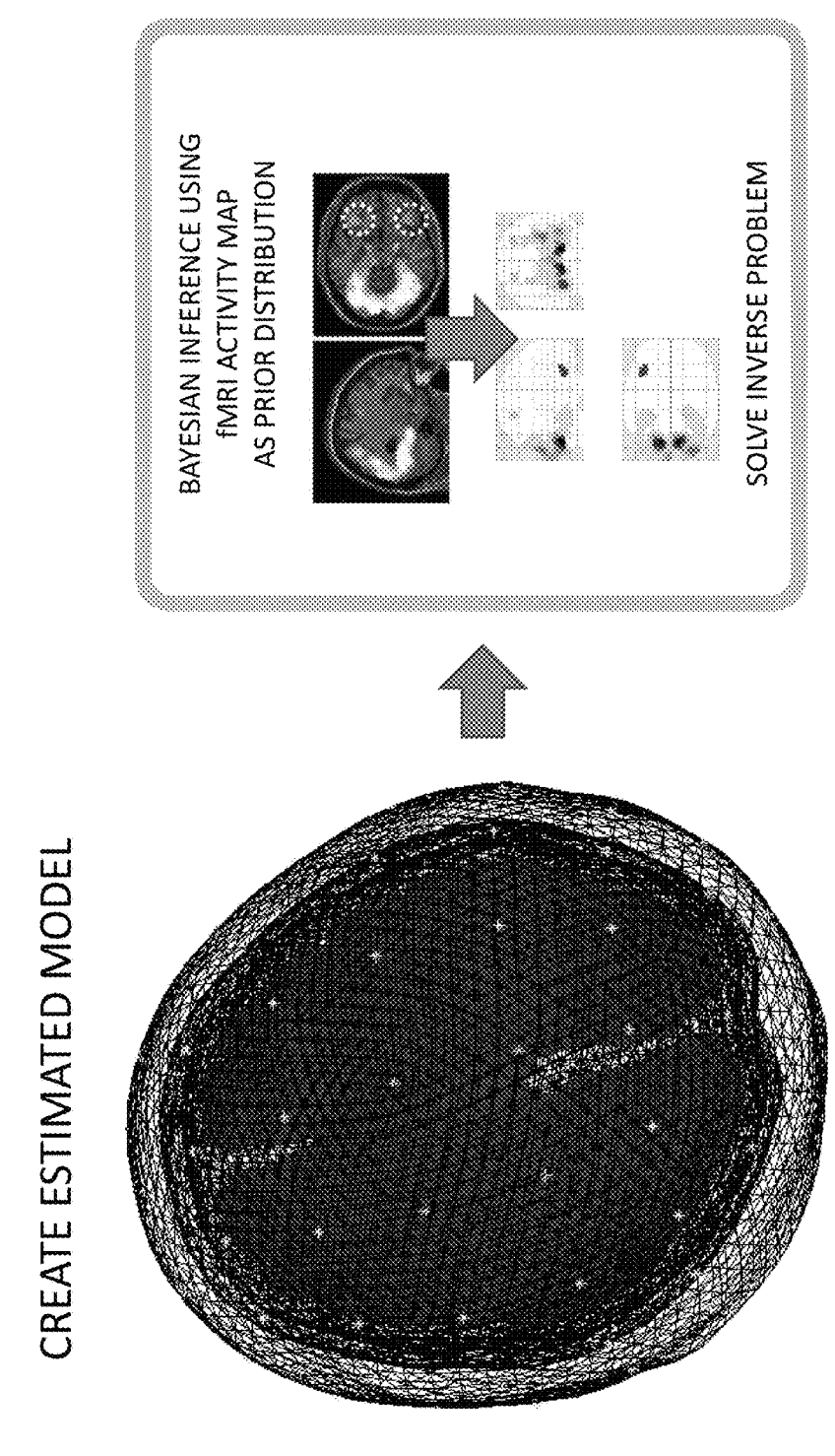
FIG. 13 shows an estimated model (forward model) in which respective brain sites are associated with EEG electrodes.

An estimated model (forward model) is created to estimate what waveform distribution would appear on the EEG electrodes arranged on the scalp (i.e., the arrangement of the electrodes positioned in Step 7) when the brain sites (i.e., nodes) on the mesh patch representing the brain structure start their activity. FIG. 13 shows, on the left-hand side, an estimated model (forward model) in which respective brain sites are associated with the EEG electrodes. This step is carried out to model a relationship between the activity of the respective nodes and the mode of appearance of electroencephalograms at the respective EEG electrodes.

[Step 9] Solving Inverse Problem by Bayesian Inference Using fMRI Activity Image as Prior Distribution The experiment with fMRI reveals that there is activity in the region of interest (i.e., the insular cortex in this example) during the pleasant image expectation and during the unpleasant image expectation. Thus, in accordance with information about sites (voxels) including the cerebral insular cortex and the forward model, the electroencephalograms measured by the EEG electrodes on the scalp are associated with the activity of the EEG signal sources. This step is carried out to associate the electroencephalograms measured by the respective EEG electrodes with the voxels in fMRI. Specifically, as shown on the right-hand side of FIG. 13, this step can be carried out by solving an inverse problem by Bayesian inference using the fMRI activity map as a prior distribution. In this case, an average cerebral activity voxel map for the pleasant image expectation, unpleasant image expectation, and unexpectable periods, obtained as a result of an fMRI experiment on 27 participants, was used and a weight was added to the voxels. Therefore, the signal sources of the electroencephalograms are estimated on the supposition that the voxels observed in fMRI should start up their activity. That is why the electroencephalograms in the region of interest can be estimated as an insular cortex signal more easily than usual. Note that Steps 5-9 described above may be performed on a known piece of software such as Statistical Parametric Mapping (Litvak, V, Mattout, J., Kiebel, S., Phillips, C., Henson, R., Kilner, J., ... Friston, K. (2011). EEG and MEG data analysis in SPM8. Computational Intelligence and Neuroscience, 2011. doi:10.1155/2011/852961).

[Step 10] Monitoring Insular Cortex Activity

Figure 14:
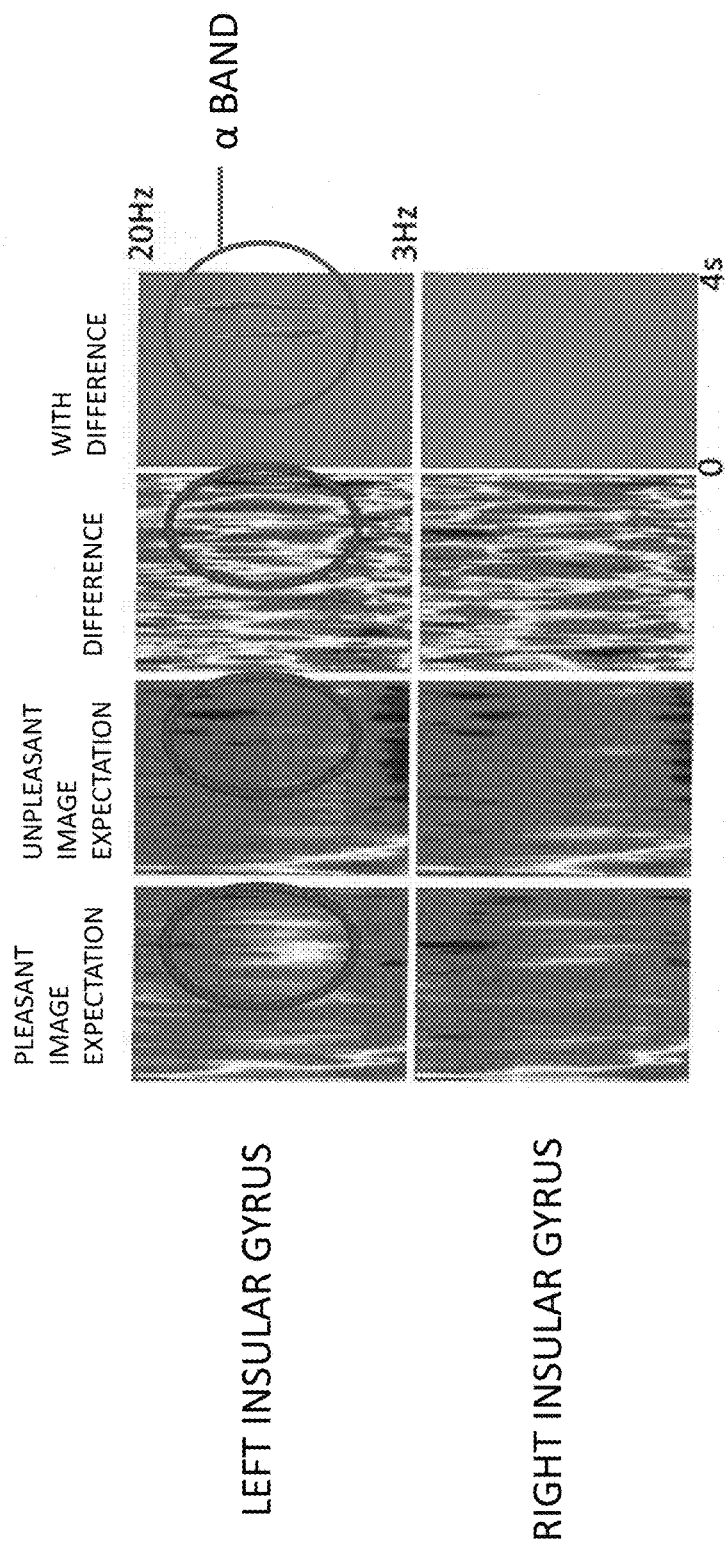
FIG. 14 shows a result of analysis on the states of left and right insular gyrus cerebral signals.

FIG. 14 shows a result of analysis on the states of left and right insular gyms cerebral signals, which was carried out to monitor the activity of the insular cortex sampled. First of all, 27 participants were made to learn in advance that a pleasant image would always be presented after the emission of tone A, an unpleasant image would always be presented to them after the emission of tone B, and either a pleasant image or an unpleasant image would be presented to them in an unexpectable way after the emission of tone C.

In this case, the results of an experiment carried out on two patterns that were pleasant image expectation in response to the emission of tone A and unpleasant image expectation in response to the emission of a tone B will be discussed. This protocol was almost the same as that of the above-described experiment for measuring the insular cortex by fMRI.

FIG. 14 shows a result was obtained by performing a time-frequency analysis on the signals of the EEG signal sources of the insular cortex sampled during the pleasant/unpleasant image expectation. As can be seen from this result, in the left insular gyms, there is a difference in the $\alpha$ band reaction between the pleasant image expectation and the unpleasant image expectation. This insular cortex activity was sampled from 24 out of the 27 subjects. That is to say, in the other four persons, no cerebral activity distributions with EEG signal sources were observed in their insular cortex.

As can be seen from the foregoing description, this embodiment provides a technique for measuring the behavior of an insular cortex using electroencephalograms, and allows the insular cortex activity at a certain point in time to be represented as numerical data based on a spectrum signal in the $\alpha$ band. In other words, this embodiment allows the pleasant image expectation and unpleasant image expectation from being distinguished from each other based on the electroencephalograms. This means that the time axis (indicating, for example, the sense of expectation) in a multi-axis sensibility (Kansei) model can be evaluated by using electroencephalograms, which are easier to measure than fMRI. This will contribute greatly toward the realization of a sensibility (Kansei) interface that links a human being to an object via sensibility (Kansei) information.

A method for sampling cerebral insular cortex activity according to the present disclosure allows for detecting the activity of an insular cortex, and evaluating the sensibility (Kansei) more accurately, based on electroencephalograms. Thus, the present disclosure is useful as a fundamental technology for realizing a sensibility (Kansei) interface that links a human being to an object via sensibility (Kansei) information.

What is claimed is:

1. A method for sampling cerebral insular cortex activity, the method comprising:
   recording electroencephalograms (EEGs) provided by a plurality of EEG electrodes;
   creating a three-dimensional model in the form of a mesh in which a subject's brain is decomposed into a plurality of sites according to the subject's brain structure and positioning the plurality of EEG electrodes by reference to an image representing the subject's brain and head structure;

creating a forward model by modeling a correlation between the activities of the respective brain sites of the three-dimensional model and an electroencephalogram distribution of the positioned EEG electrodes;

estimating, by reference to information about a region of interest measured by functional magnetic resonance imaging (fMRI) and the forward model, signal sources of the EEGs associated with the cerebral activity of the region of interest, the region of interest measured by fMRI being an insular cortex that starts cerebral activity when the subject is expecting a presentation of a pleasant image or an unpleasant image but without actual presentation of the pleasant image or the unpleasant image;

performing a time-frequency analysis on signals of the signal sources of the EEGs to obtain a spectrum signal, the spectrum signal being based on a first signal measured over a pleasant image expectation period and a second signal measured over an unpleasant image expectation period; and representing the cerebral activity of the region of interest as numerical data based on the spectrum signal in an α band, wherein the numerical data includes a time-frequency difference between the first signal of the pleasant image expectation period and the second signal of the unpleasant image expectation period.

2. The method of claim 1, wherein recording the electroencephalograms includes decomposing the recorded electroencephalograms provided by the plurality of EEG electrodes into a plurality of independent components, removing unnecessary ones of the independent components, and back-projecting the rest of the independent components, other than the unnecessary ones, on an EEG electrode basis to generate electroencephalogram information about the EEG electrodes.

3. The method of claim 1, wherein the forward model is created by modeling a correlation between the activities of respective brain sites of the three-dimensional model in the form of a mesh and appearance of electroencephalograms to the respective EEG electrodes.

4. The method of claim 2, wherein the region of interest measured by fMRI is an insular cortex starting cerebral activity when a pleasant image is expected and when an unpleasant image is expected.

5. The method of claim 2, wherein the forward model is created by modeling a correlation between the activities of respective brain sites of the three-dimensional model in the form of a mesh and appearance of electroencephalograms to the respective EEG electrodes.

6. The method of claim 1, wherein the forward model is created by modeling a correlation between the activities of respective brain sites of the three-dimensional model in the form of a mesh and appearance of electroencephalograms to the respective EEG electrodes.

7. The method of claim 4, wherein the forward model is created by modeling a correlation between the activities of respective brain sites of the three-dimensional model in the form of a mesh and appearance of electroencephalograms to the respective EEG electrodes.

* * * * *